(12) United States Patent
Kawaguchi

(10) Patent No.: US 6,845,263 B2
(45) Date of Patent: Jan. 18, 2005

(54) HEART-SOUND DETECTING APPARATUS AND PULSE-WAVE-PROPAGATION-VELOCITY-RELATING-INFORMATION OBTAINING SYSTEM USING THE HEART-SOUND DETECTING APPARATUS

(75) Inventor: Keizoh Kawaguchi, Komaki (JP)

(73) Assignee: Colin Medical Technology Corporation, Komaki (JP)

(*) Notice: Subject to any disclaimer, the term of this patent is extended or adjusted under 35 U.S.C. 154(b) by 307 days.

(21) Appl. No.: 09/895,178

(22) Filed: Jul. 2, 2001

(65) Prior Publication Data

US 2003/0009108 A1 Jan. 9, 2003

(51) Int. Cl.[7] ............................................. A61B 5/02
(52) U.S. Cl. ...................... 600/513; 600/504; 600/528
(58) Field of Search ............................ 600/487, 504, 600/508, 509, 513, 528, 586; 128/901–902

(56) References Cited

U.S. PATENT DOCUMENTS

| 4,549,552 A | * | 10/1985 | Groch et al. | 600/513 |
| 5,237,997 A | * | 8/1993 | Greubel et al. | 600/485 |
| 5,293,874 A | * | 3/1994 | Takahashi et al. | 600/500 |
| 5,309,917 A | * | 5/1994 | Wang et al. | 600/508 |
| 6,120,456 A | | 9/2000 | Oka et al. | |
| 6,315,734 B1 | * | 11/2001 | Nunome | 600/500 |
| 2002/0035337 A1 | * | 3/2002 | Oka | 600/528 |

FOREIGN PATENT DOCUMENTS

| EP | 0 498 281 A1 | 8/1992 |
| EP | 1 095 611 A1 | 5/2001 |
| JP | A 8-257002 | 10/1996 |

* cited by examiner

Primary Examiner—Kennedy Schaetzle
Assistant Examiner—Kristen Mullen
(74) Attorney, Agent, or Firm—Oliff & Berridge, PLC

(57) ABSTRACT

A heart-sound detecting apparatus, including: a heart-sound microphone which detects a plurality of heart sounds produced by a heart of a living subject and outputs a heart-sound signal representative of the detected heart sounds; a smoothing device for smoothing, by differentiation, a waveform of the heart-sound signal output from the heart-sound microphone; a squaring device for squaring an amplitude of the smoothed waveform with respect to a base line of the heart-sound signal; and a start-point determining device for determining a start point of a first heart sound I as one of the detected heart sounds, based on that the squared amplitude is greater than a prescribed threshold value.

7 Claims, 4 Drawing Sheets

HEART-SOUND DETECTING APPARATUS AND PULSE-WAVE-PROPAGATION-VELOCITY-RELATING-INFORMATION OBTAINING SYSTEM USING THE HEART-SOUND DETECTING APPARATUS

BACKGROUND OF THE INVENTION

1. Field of Invention

The present invention relates to a heart-sound detecting apparatus which can accurately determine a start point of a first heart sound I of a living subject, and a pulse-wave-propagation-velocity-relating information obtaining system using the heart-sound detecting apparatus.

2. Description of Related Art

A first heart sound I as one of a plurality of heart sounds produced by the heart of a living subject occurs upon closure of mitral valve and tricuspidalis valve. Accordingly, the first half portion of the first heart sound I includes, as a major component, closure sounds of mitral valve and triculspidalis valve, while the second half portion of the first heart sound I includes a component resulting from opening of aortic valve, which overlaps the first half portion of the first heart sound I resulting from the closure of mitral valve and tricuspidalis valve.

The heart sounds are influenced by internal noise such as blood-flow sound, and background or external noise which occurs outside the living subject. Accordingly, a waveform of heart-sound signal which represents the first heart sound I has a complicated shape, making it difficult to accurately determine a start point of the first heart sound I.

SUMMARY OF THE INVENTION

Therefore the present invention provides a heart-sound detecting apparatus which can accurately determine the start point of the first heart sound I.

According to a first feature of the present invention, there is provided a heart-sound detecting apparatus, including: a heart-sound microphone which detects a plurality of heart sounds produced by a heart of a living subject and outputs a heart-sound signal representative of the detected heart sounds; a smoothing device for smoothing, by differentiation; a waveform of the heart-sound signal output from the heart-sound microphone; a squaring device for squaring an amplitude of the smoothed waveform with respect to a base line of the heart-sound signal; and a start-point determining device for determining a start point of a first heart sound I as one of the detected heart sounds, based on that the squared amplitude is greater than a prescribed threshold value.

The heart-sound signal output from the heart-sound microphone includes a low-frequency noise, and has an alternating waveform including positive amplitudes and negative amplitudes on both sides of a base line thereof. In the present heart-sound detecting apparatus, the smoothing device smoothes, by differentiation, a waveform of the heart-sound signal output from the heart-sound microphone, and provides a smoothed waveform in the form of a differential waveform which shows a clear change of amplitudes. In addition, the squaring device squares an amplitude of the smoothed waveform with respect to a base line of the heart-sound signal, and provides a squared waveform having the squared amplitude on only the positive side of the base line. The start-point determining device determines a start point of the first heart sound I, based on that the squared amplitude is greater than a prescribed threshold value. Accordingly, the present heart-sound detecting apparatus can accurately determine the start point of the first heart sound I.

According to a second feature of the present invention, the heart-sound detecting apparatus further includes a high-pass filter which passes a component of the heart-sound signal output from the heart-sound microphone, the component having frequencies which are not lower than a lowest signal-pass frequency of the high-pass filter that is lower, by not less than a prescribed value, than a lowest frequency of the first heart sound I, wherein the smoothing device smoothes, by differentiation, the component of the heart-sound signal which has passed through the high-pass filter. According to this arrangement, the waveform of the heart-sound signal is subjected to the differentiating-smoothing process and the squaring process after the high-pass filter has removed the low-frequency noise included in the heart-sound signal and having frequencies which are lower, by not less than a prescribed value, than the lowest frequency of the first heart-sound I. Therefore, the start point of the first sound I can be accurately determined.

According to a third feature of the present invention, the heart-sound detecting apparatus further includes an electrocardiograph which includes a plurality of electrodes adapted to be worn at a plurality of locations on the subject and which detects, through the electrodes, an electrocardiogram of the subject, wherein the start-point determining device determines, as a start point of a judging period to judge whether the squared amplitude is greater than the prescribed threshold value, a time point during a time period between a Q-wave and an R-wave of the electrocardiogram detected by the electrocardiograph, and determines, during the judging period, the start point of the first heart sound I based on a judgment that the squared amplitude is greater than the prescribed threshold value. Since the first heart-sound I occurs following occurrence of the R-wave of the electrocardiogram detected by the electrocardiograph, the present arrangement assures an accurate determination of the start-point of the first heart-sound I.

According to a fourth feature of the present invention, there is provided a system for obtaining information relating to a propagation velocity at which a pulse wave propagates along an artery of a living subject, the system including: a heart-sound detecting apparatus according to any one of the above-described features first to third features; a pulse-wave detecting device which is adapted to be worn on the subject to detect the pulse wave which propagates along the artery of the subject; and a pulse-wave-propagation-velocity-relating-information obtaining device for obtaining the information based on a time of the start point of the first heart sound I determined by the start-point determining device of the heart-sound detecting apparatus, and a time when a rising point of the pulse wave is detected by the pulse-wave detecting device.

The information relating to the pulse-wave propagation velocity may be the pulse-wave propagation velocity itself, or a pulse-wave propagation time.

In the present pulse-wave-propagation-velocity-relating-information obtaining system, the start-point determining device of the heart-sound detecting apparatus accurately determines the start point of the first heart sound I, and the pulse-wave-propagation-velocity-relating-information obtaining device obtains the pulse-wave-propagation-velocity-relating information, based on the accurately determined start point of the heart sound I and a timing when the rising point of the pulse wave is detected by the pulse-wave

BRIEF DESCRIPTION OF THE DRAWINGS

The above and optional objects, features, and advantages of the present invention will be better understood by reading the following detailed description of exemplary embodiments of the invention when considered in conjunction with the accompanying drawings, in which.

DETAILED DESCRIPTION OF PREFERRED EMBODIMENTS

Figure 1:
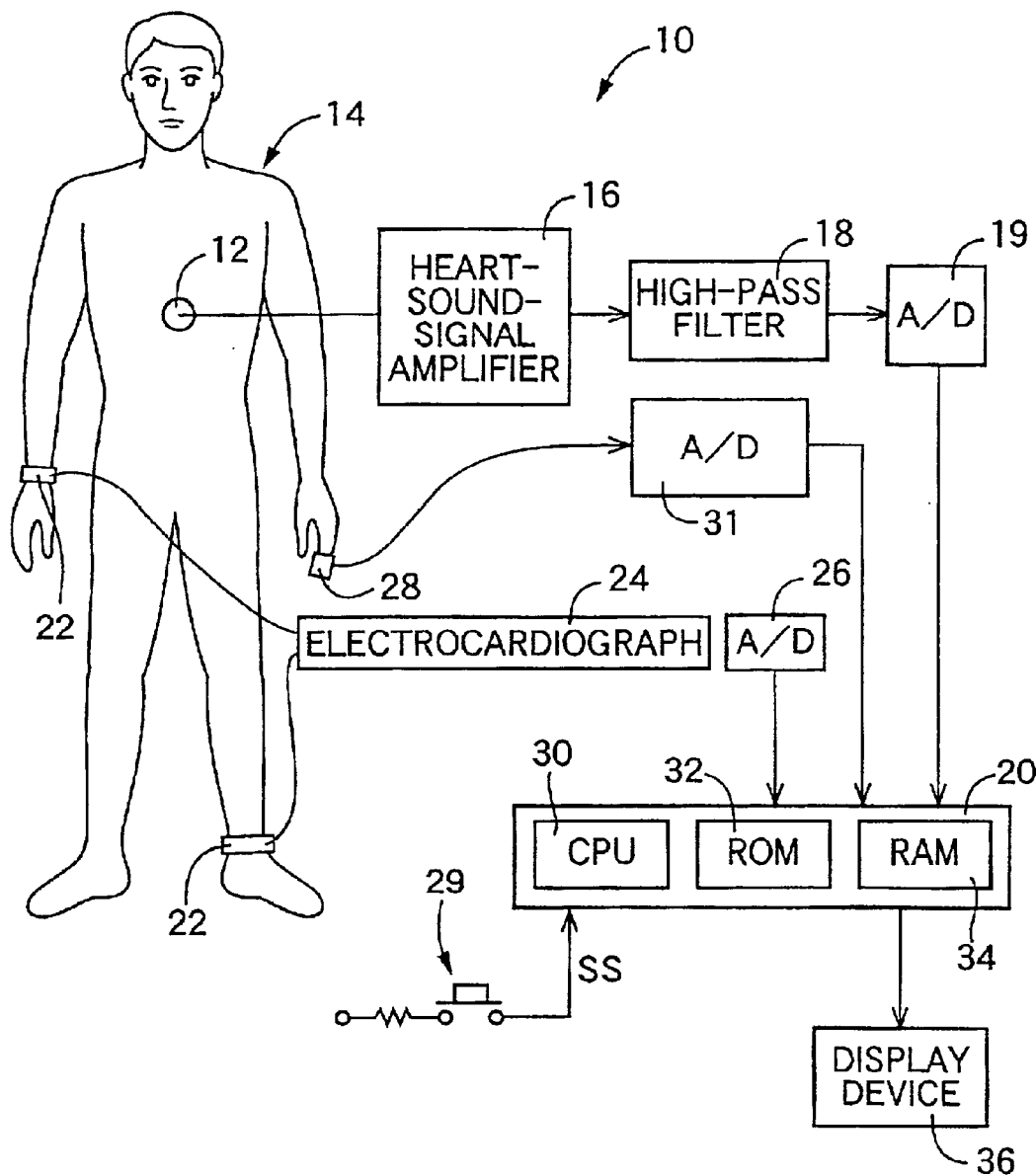
FIG. 1 is a diagrammatic view for explaining a construction of a pulse-wave-propagation-velocity-relating-information obtaining system including a heart-sound detecting apparatus, to which the present invention is applied.

Hereinafter, there will be described an embodiment of the present invention, by reference to the drawings. FIG. 1 is a diagrammatic view for explaining the construction of a pulse-wave-propagation-velocity-relating-information obtaining system 10 functioning as a heart-sound detecting apparatus, to which the present invention is applied.

In FIG. 1, the present system 10 includes an acceleration-type heart-sound microphone 12 which is fixed, with an adhesive tape, not shown, to a prescribed location on a chest of a living subject 14. The microphone 12 accommodates a piezoelectric element, not shown, which converts heart sounds produced from the heart of the subject 14, into an electric signal, i.e., heart-sound signal SH. A heart-sound signal amplifier 16 includes four sorts of filters, not shown, which cooperate with one another to attenuate a low-pitch component having a great energy and thereby amplifies and filters a high-pitch component of the heart-sound signal SH.

The heart-sound signal output from the amplifier 16 is supplied to a high-pass filter 18. In the present embodiment, the lowest signal-pass frequency $f_L$ of the high-pass filter 18 is set at 60 Hz, so that the component of the heart-sound signal SH having frequencies not lower than 60 Hz is passed through the high-pass filter 18 without being attenuated. The high-pass filter 18 is adapted to remove low-frequency noise included in the heart-sound signal SH output from the microphone 12, mainly, internal noise such as blood-flow sound, and pass the first heart-sound I without attenuating it. In view of this, the lowest signal-pass frequency $f_L$ of the high-pass filter 18 is determined to be lower, by not less than a prescribed value α, than the lowest frequency of the first heart sound I. The prescribed value α is determined to be about 0~10 Hz. In the present embodiment, therefore, the lowest signal-pass frequency $f_L$ of the high-pass filter 18 is about 60 Hz~80 Hz since the lowest frequency of the first heart sound I is generally in a range of about 70 Hz~80 Hz.

The heart-sound signal SH output from the high-pass filter 18 is supplied to an electronic control device 20 via an analog-to-digital (A/D) converter 19.

Figure 2:
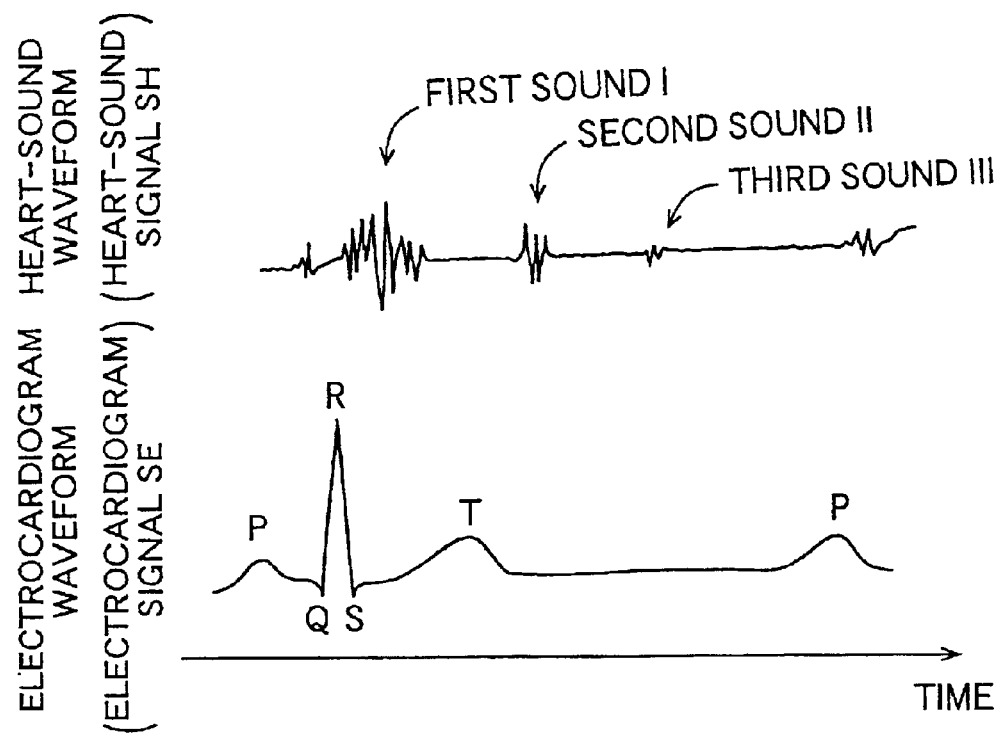
FIG. 2 is a graph showing an electrocardiogram and a heart-sound wave which are detected by an electrocardiograph and a microphone of the system of FIG. 1.

An electrocardiograph 24 includes two electrodes 22 which are adapted to be worn on respective body portions of the subject 14 that are distant from each other via the heart, and which cooperate with each other to provide an electrocardiogram signal SE representing an action potential of the cardiac muscle of the subject 14. In the present embodiment, the two electrodes 22 are worn on a right wrist and a left ankle of the subject 14, respectively, to provide a two-electrode-induced electrocardiogram. The electrocardiogram signal SE produced from the electrodes 22 is amplified by an amplifier, not shown, of the electrocardiograph 24, and then is supplied to the control device 20 via an A/D converter 26. FIG. 2 shows a waveform of the heart sounds detected by the microphone 12, and a waveform of the electrocardiogram detected by the electrocardiograph 24.

A photoelectric-pulse-wave sensor 28 functions as a pulse-wave detecting device which detects a pulse wave propagated to peripheral arterioles including capillaries, and may have a construction similar to that of one which is used to detect pulse. The sensor 28 is worn on a body portion (e.g., an end portion of a finger) of the subject 14. The sensor 28 includes a housing, not shown, which can accommodate a body portion of the subject 14; a light emitting element, not shown, as a light source which emits, toward a skin of the subject 14, a red or infrared light in such a wavelength band that can be reflected by hemoglobin, preferably a light having a wavelength of about 800 nm that is not influenced by blood oxygen saturation; and a light receiving element, not shown, which detects the light scattered from the body portion under the skin. The sensor 28 outputs a photoelectric-pulse-wave signal SM representing respective instantaneous volumes of the blood present in the capillaries of the body portion, and supplies the signal SM to the control device 20 via an A/D converter 31. The photoelectric-pulse-wave signal SM changes or pulsates in synchronism with each heartbeat of the subject 14, and represents the instantaneous amount of the hemoglobin present in the capillaries of the body portion under the skin, i.e., the volume of the blood present in the capillaries. The photoelectric-pulse-wave signal SM includes a rising point at which magnitude of the signal SM abruptly increases. The rising point of the signal SM corresponds to the first heart-sound I.

A push button 29 supplies, when being pushed by an operator, a start signal SS to the control device 20.

The control device 20 is essentially provided by a so-called microcomputer including a central processing unit (CPU) 30, a read only memory (ROM) 32, a random access memory (RAM) 34, an input-and-output (I/O) port, not shown, etc. The control device 20 or the CPU 30 processes signals according to control programs pre-stored in the ROM 32, while utilizing a temporary-storage function of the RAM 34, and thereby iteratively determines a start point of the first heart sound I, i.e., a timing when the first heart sound I starts, and iteratively obtains a piece of pulse-wave-propagation-velocity-relating information. In addition, the CPU 30 operates a display device 36 to display iteratively the obtained pulse-wave-propagation-velocity-relating information.

Figure 3:
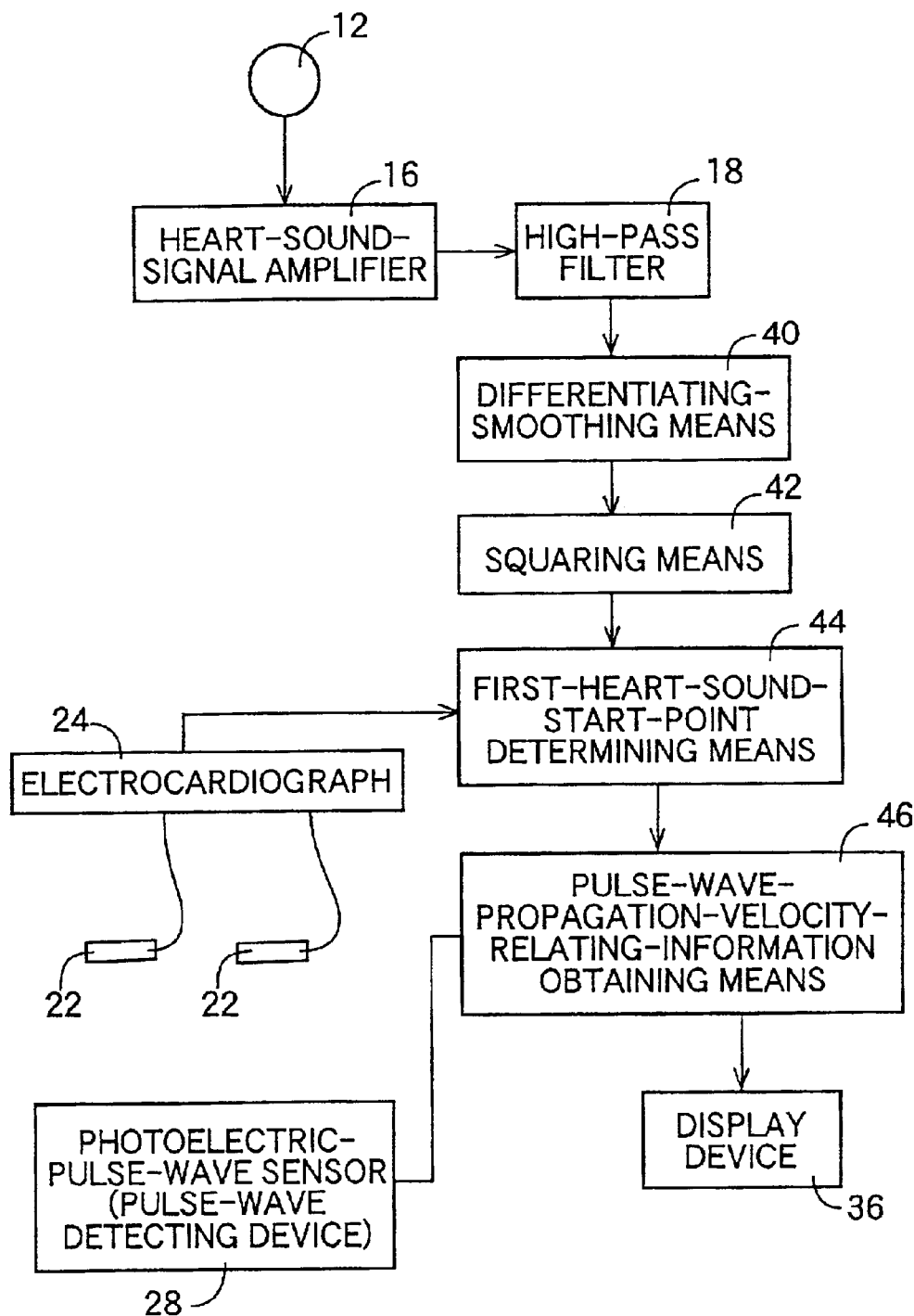
FIG. 3 is a block diagram for explaining essential functions of an electronic control device of the system of FIG. 1.

FIG. 3 is a block diagram for explaining essential functions of the control device 20 of the information obtaining system 10. In the figure, a differentiating-smoothing device 40 differentiates, and thereby smoothes, the waveform of the heart-sound signal SH detected by the microphone 12. In the differentiating-smoothing process, each of data points of the heart-sound signal SH that are sequentially input is differentiated by obtaining a linear sum of central differences, according to the following expression (1) pre-stored in the

ROM 32:

$$y_{(k)} = d/2 \cdot \sum_{n=1}^{N} C_n \{x_{(k+n)} - x_{(k-n)}\} \quad (1)$$

where d is a value determined based on a sampling period T; N is a degree; and $C_n$ is a coefficient.

For example, d=1/T, N=1, and $C_1$=1. The above expression (1) indicates that the differentiating-smoothing process consists of only low-degree adding and subtracting calculations. Since this process is widely applicable, it is known as a useful process for dealing with a signal obtained from a living subject.

A squaring device 42 determines respective amplitudes or magnitudes of data points of the waveform, smoothed by the differentiating-smoothing device 40, with respect to a base line of the waveform, and squares the respective amplitudes of the data points. The heart-sound signal SH output from the microphone 12 is an alternating waveform having positive amplitudes and negative amplitudes on both sides of its base line which indicates a level of the heart-sound signal when no heart sounds are detected by the microphone 12. Accordingly, the differentiated waveform provided by the differentiating-smoothing device 40 is also an alternating waveform having positive and negative amplitudes on both sides of its base line. Since the amplitudes of the alternating waveform may increase on each of the positive and negative sides of the base line, it is not so easy to determine, based on the alternating waveform, a timing when the first heart-sound I starts. Hence, the alternating waveform is subjected to the squaring process so as to provide a waveform having amplitudes on only the positive side of its base line. In addition, since the components resulting from the heart sounds have amplitudes greater than that of noise, a difference between the respective amplitudes of the components resulting from the heart sounds and the amplitude of noise is amplified by the squaring process. Thus, the waveform provided by the squaring device 42 shows a clear point indicating a timing when the first heart-sound I starts.

A start-point determining device 44 determines a start point of the first heart sound I, based on that the amplitude or magnitude of each of the data points is greater than a threshold value TH which is experimentally obtained in advance. The start-point determining device 44 determines, as a start point of a judging period to judge whether the squared amplitude of each data point is greater than the threshold value TH, based on the electrocardiogram detected by the electrocardioraph 24. As shown in FIG. 2, the first heart-sound I occurs following occurrence of the R-wave of the electrocardiogram. By determining, as the start point of the judging period described above, any time point during a time period between occurrence of the Q-wave and occurrence of the R-wave (e.g., a point of occurrence of the Q-wave or the R-wave), the determining device 44 does not erroneously identify, as the start point of the first heart-sound I, noise component which may be present in the heart signal SH detected before the start point of the judging period and which was not removed from the signal SH by the high-pass filter 18, differentiating-smoothing device 40, and squaring device 42. Since a time interval between the occurrence of the Q-wave of the elcectrocardiogram and the occurrence of the first heart sound I is very short, there is little chance to detect noise, during the time interval, which is not removed by the high-pass filter 18, differentiating-smoothing device 40, and squaring device 42.

A pulse-wave-propagation-velocity-relating-information obtaining device 46 includes a pulse-wave-propagation-time determining device which iteratively determines a time difference between the start point of the heart sound 1, determined by the start-point determining device 44, and a timing when the rising point of the photoelectric pulse wave is detected by the photoelectric-pulse-wave sensor 28, as a propagation time DT (second) which is needed for the pulse wave to propagate from the heart to a position where the sensor 28 is worn on the subject 14. The information obtaining device 46 iteratively calculates, based on each of the pulse-wave propagation time values DT iteratively determined by the pulse-wave-propagation-time determining device, a pulse-wave propagation velocity PWV (m/sec) at which the pulse wave propagates through an artery of the subject 14, according to the following expression (2) pre-stored in the ROM 32:

$$PWV=L/DT \quad (2)$$

where L (m) is the propagation distance from the initial portion of the aorta to the position where the sensor 28 is worn.

In the above expression (2), L is a constant which is experimentally obtained in advance. The information obtaining device 46 iteratively operates the display device 36 to display iteratively each of the pulse-wave propagation velocity values PWV determined thereby.

Figure 4:
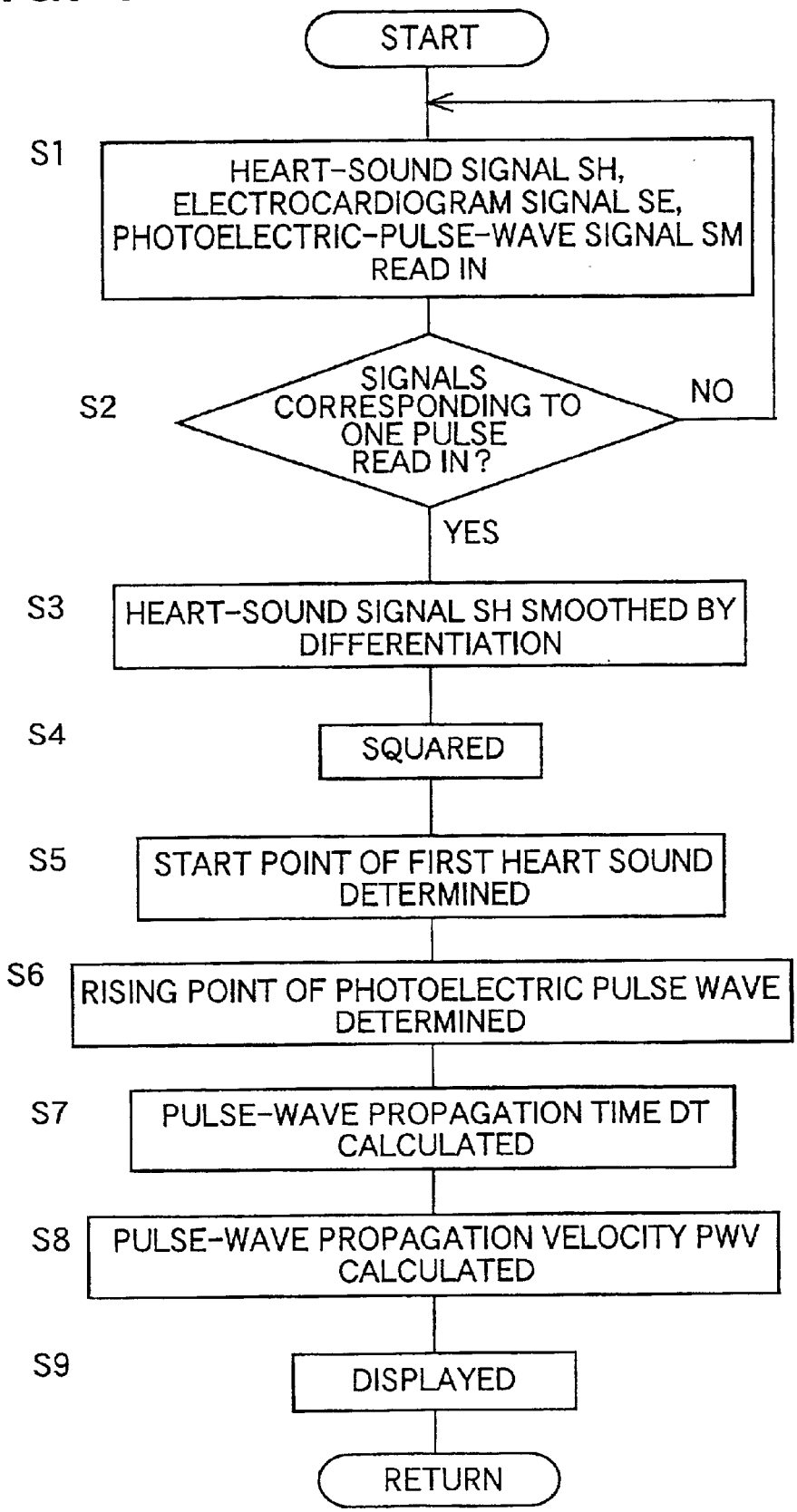
FIG. 4 is a flow chart representing a control program according to which the control device shown in the block diagram of FIG. 3 controls the system of FIG. 1.

FIG. 4 is a flow chart for explaining the essential functions of the control device 20, illustrated in the block diagram of FIG. 3. A control routine according to this flow chart is started when the push button 29 is pushed and a start signal SS is supplied from the button 29 to the control device 20.

Then, at S2, the control device 20 judges, based on the Q-wave of the electrocardiogram signal SE, for instance, whether the control device 20 has already read in, at S1, the heart-sound signal SH, the electrocardiogram signal SE, and the photoelectric-pulse-wave signal SM that correspond to one-time pulse of the subject 14. If a negative judgment is made at S2, S1 is repeated to continue reading in the heart-sound signal SH, the electrocardiogram signal SE, and the photoelectric-pulse-wave signal SM.

On the other hand, if a positive judgment is made at S2, the control of the control device 20 proceeds with S3 corresponding to the differentiating-smoothing device 40, to replace the variables $x_{(k+n)}$, $x_{(k-n)}$ of the expression (1), with the data points of the heart-sound signal SH, read in at S1 and S2, and thereby differentiates or smoothes the signal SH. Thus, the differentiated waveform of the heart-sound signal SH is provided. In the expression (1), for example, d, N, and $C_n$ is such that d=I/T, N=1, and $C_1$=1.

Subsequently, at S4 corresponding to the squaring device 42, the control device 20 squares the respective amplitudes of respective data points of the differentiated or smoothed waveform obtained at S3. More specifically described, the control device 20 squares the respective amplitudes of respective data points of the smoothed waveform with respect to the base line of the waveform.

Then, at S5 corresponding to the start-point determining device 44, the control device 20 determines a time point corresponding to the occurrence of the Q-wave of the electrocardiogram in the data points of the heart-sound signal SH read in at S1 and S2. Within a certain time duration (e.g., 100 msec) as measured from the occurrence of the Q-wave, the control device 20 judges whether each of the respective amplitudes or magnitudes of the respective data points of the squared waveform obtained at step S4 is greater than a prescribed threshold value TH, and determines, as a start point of the first heart sound I, a time corresponding to a point on the squared waveform where the respective amplitudes or magnitudes of data points of the waveform first exceed the prescribed threshold value TH after the occurrence of the Q-wave.

Then, at S6, the control device 20 determines, based on the photoelectric-pulse-wave signal SM read in at S1, a timing when a rising point of the photoelectric pulse wave is detected by the photoelectric-pulse-wave sensor 28. S6 is followed by S7 and S8 corresponding to the pulse-wave-propagation-velocity-relating-information obtaining device 46.

First, at S7, the control device 20 determines, as a pulse-wave propagation time DT, a time difference between the start point of the first heart sound I determined at S5 and the timing of detection of the rising point of the photoelectric pulse wave determined at S6. S7 is followed by S8 where the control device 20 replaces the variable DT of the expression (2), with the pulse-wave propagation time DT determined at S7, and thereby calculates a pulse-wave propagation velocity PWV.

S8 is followed by S9 where the control device 20 operates the display device 36 to display the pulse-wave propagation velocity PWV calculated at S8.

In the illustrated embodiment, the differentiating-smoothing device 40 differentiates and thereby smoothes, at S3, the waveform of the heart-sound signal SH detected by the microphone 12, and provides a smoothed waveform of the heart-sound signal SH in the form of a differentiated waveform showing a clear amplitude change. In addition, the squaring device 42 squares, at S4, the respective amplitudes or magnitudes of data points of the waveform, processed by the differentiating-smoothing device 40 at S3, with respect to the base line of the waveform, and provides a waveform having amplified amplitudes on only the positive side of its base line. And, the start-point determining device 44 determines, at S5, as a start point of the first heart sound I, a time corresponding to a point on the squared waveform where the respective amplitudes or magnitudes of data points of the waveform first exceed the prescribed threshold value TH during the judging period to judge whether the amplitude or magnitude of each of the data points of the squared waveform is greater than the threshold value TH. Therefore, the present system 10 can more accurately determine a start point of the first heart sound I.

In the illustrated embodiment, the heart-sound signal SH is subjected to the differentiating-smoothing process and the squaring process after the high-pass filter 18 has removed therefrom the low-frequency noise whose frequency is not higher than 60 Hz. Accordingly, the start point of the first heart sound I can be accurately determined.

The pulse-wave-propagation-velocity-information obtaining system 10 of the illustrated embodiment includes the electrocardiograph 24 which includes the two electrodes 22 adapted to be worn on a right wrist and a left ankle of the subject 14, respectively, and which detects, through the electrodes, the electrocardiogram of the subject 14. The start-point determining device 44 determines, at S5, as a start point of a judging period to judge whether the amplitude of each of the data points of the squared waveform is greater than the threshold value TH, a time point corresponding to the occurrence of the Q-wave of the electrocardiogram signal SE. And, the start-point determining device 44 determines, during the judging period, the start point of the first hear sound I based on a judgment that the squared amplitude is greater than the threshold value TH. Accordingly, the start-point of the first heart sound I can be accurately determined.

In the illustrated embodiment, the start point of the first heart sound I is accurately determined by the start-point determining device 44 at S5, and the pulse-wave-propagation-velocity-relating-information obtaining device 46 (corresponding to S7 and S8) accurately determines a pulse-wave propagation velocity PVW and a pulse-wave propagation time DT, based on the accurately determined start point of the first heart sound I and the timing when the rising point the photoelectric-pulse-wave signal SM is detected by the photoelectric-pulse-wave sensor 28.

While the present invention has been described in detail in its embodiment, by reference to the drawings, the invention may otherwise be embodied.

The pulse-wave-propagation-velocity-relating-information obtaining system 10 of the illustrated embodiment is provided with the high-pass filter 18 to remove the low-frequency noise from the heart-sound signal SH. The high-pass filter 18 may be eliminated since the differentiating-smoothing device 40 (corresponding to S3) removes the low-frequency noise from the heart-sound signal SH.

The microphone 12 employed in the system 10 is of acceleration type. However, the microphone 12 may be any other sort of microphone, such as airborne type, pendent type, or placement type.

The system 10 of the illustrated embodiment includes the electrocardiograph 24 which includes the two electrodes 22 and which detects, through the electrodes, the electrocardiogram of the subject 14. The start-point determining device 44 (corresponding to S5) determines, as the start point of the judging period to judge whether the amplitude of each of the data points of the squared waveform is greater than the threshold value TH, a time point corresponding to the occurrence of the Q-wave of the electrocardiogram signal SE. If the start point of the judging period is determined based on the heart-sound signal SH itself or the photoelectric-pulse-wave signal SM, the system 10 may not have the electrodes 22 and the electrocardiograph 24. In this case, the system 10 can be obtained at a reduced cost.

In addition, in the illustrated pulse-wave-propagation-velocity-relating-information obtaining system 10, the photoelectric-pulse-wave sensor 28 which is worn on an end portion of a finger of the subject 14 is employed as a pulse-wave detecting device. However, a pressure-pulse-wave sensor which is pressed against a prescribed portion of a living subject and detects a pressure pulse wave propagated to the body portion, a pressure-pulse-wave sensor which includes a pressing band adapted to be worn on a prescribed portion (e.g., upper arm) of a living subject and detects a change of a pressure in the pressing band, a photoelectric-pulse-wave detecting probe for use with an oximeter, or an impedance-pulse-wave detecting device which detects an impedance change through electrodes worn on a finger of a living subject may be employed as the pulse-wave detecting device.

In addition, in the illustrated embodiment, the start-point determining device 44 (S5) determines, during the judging period determined based on the electrocardiogram signal SE, whether the amplitude of each data point of the squared waveform provided by the squaring device 42 is greater than the prescribed threshold value TH. The amplitudes or magnitudes of the data points of the squared waveform are kept at a relatively large level during a certain time period corresponding to a time duration in which the first heart sound I occurs. In view of this, the start-point determining device 44 may identify the time period as the first heart sound I, based on that the time period in which the amplitudes or magnitudes of the data points of the squared waveform are greater than the threshold value TH lasts longer than a prescribed time duration. In this case, the start-point determining device 44 determines, as a start point of the heart sound I, a beginning of the time period. Moreover, the start-point determining device 44 may determine the start point of the judging period, based on a characteristic point of the heart-sound signal SH or a characteristic point of the photoelectric-pulse-wave signal SM (e.g., a rising point).

It is to be understood that the present invention may be embodied with other changes, improvements and modifications that may occur to one skilled in the art without departing from the spirit and scope of the invention.

What is claimed is:

1. A system for obtaining information relating to a propagation velocity at which a pulse wave propagates along an artery of a living subject, the system comprising:
   a heart-sound detecting apparatus comprising:
      a heart-sound microphone which detects a plurality of heart sounds produced by a heart of a living subject and outputs a heart-sound signal representative of the detected heart sounds;
      a smoothing device for smoothing, by differentiation, a waveform of the heart-sound signal output from the heart-sound microphone;
      a squaring device for squaring an amplitude of the smoothed waveform with respect to a base line of the heart-sound signal; and
      a start-point determining device for determining a start point of a first heart sound I as one of the plurality of detected heart sounds, based on that the squared amplitude being greater than a prescribed threshold value;
   a pulse-wave detecting device which is adapted to be worn on the subject to detect the pulse wave which propagates along the artery of the subject; and
   a pulse-wave-propagation-velocity-relating-information obtaining device for obtaining information based on a time of the start point of the first heart sound I determined by the start-point determining device of the heart-sound detecting apparatus, and a time when a rising point of the pulse wave is detected by the pulse-wave detecting device.

2. The system according to claim 1, wherein the pulse-wave-propagation-velocity-relating-information obtaining device, comprises:
   a pulse-wave-propagation-time determining device for determining, based on the time of the start point of the first heart sound I, and the time when the rising point of the pulse wave is detected by the pulse-wave detecting device, a propagation time needed for the pulse wave to propagate from the heart to a position where the pulse-wave detecting device is worn on the subject.

3. The system according to claim 1, wherein the pulse-wave-propagation-velocity-relating-information obtaining device comprises:
   a pulse-wave-propagation-velocity determining device for determining the propagation velocity at which the pulse wave propagates, by dividing a distance from the heart to a position where the pulse-wave detecting device is worn on the subject by a time difference between the time of the start point of the first heart sound I and the time when the rising point of the pulse wave is detected by the pulse-wave detecting device.

4. The system according to claim 1, further comprising:
   an output device which outputs the information obtained by the pulse-wave-propagation-velocity-relating-information obtaining device, so that an observer can observe the output information.

5. The system according to claim 1, wherein said heart-sound detecting apparatus further comprises:
   a high-pass filter which passes a component of the heart-sound signal output from the heart-sound microphone, the component having frequencies which are not lower than a lowest signal-pass frequency of the high-pass filter that is lower, by not less than a prescribed value, than a lowest frequency of the first heart sound I, wherein the smoothing device smoothes, by differentiation, the component of the heart-sound signal which has passed through the high-pass filter.

6. The system according to claim 1, wherein said heart-sound detecting apparatus further comprises:
   an electrocardiograph which includes a plurality of electrodes adapted to be worn at a plurality of locations on the subject and which detects, through the electrodes, an electrocardiogram of the subject, wherein the start-point determining device determines, as a start point of a judging period to judge whether the squared amplitude is greater than the prescribed threshold value, a time point during a time period between a Q-wave and an R-wave of the electrocardiogram detected by the electrocardiograph, and determines, during the judging period, the start point of the first heart sound I based on a judgment that the squared amplitude is greater than the prescribed threshold value.

7. The system according to claim 1, wherein the squaring device squares an amplitude of each of a plurality of data points on the smoothed waveform with respect to the base line of the heart-sound signal, and the start-point determining device determines the start point of the first heart sound I based on that the squared amplitude of said each data point is greater than the threshold value.

* * * * *